(12) United States Patent
Yu et al.

(10) Patent No.: US 8,148,386 B2
(45) Date of Patent: Apr. 3, 2012

(54) AGENT FOR THE PREVENTION AND TREATMENT OF PROSTATIC HYPERPLASIA COMPRISING PYRAZOLOPYRIMIDINONE COMPOUND

(75) Inventors: Jae Young Yu, Kyunggi-do (KR); Seul Min Choi, Kyunggi-do (KR); Kyung Koo Kang, Kyunggi-do (KR); Byoung Ok Ahn, Kyunggi-do (KR); Moohi Yoo, Seoul (KR)

(73) Assignee: Dong-A Pharmtech Co., Ltd., Seoul (KR)

( * ) Notice: Subject to any disclaimer, the term of this patent is extended or adjusted under 35 U.S.C. 154(b) by 492 days.

(21) Appl. No.: 12/244,432

(22) Filed: Nov. 24, 2008

(65) Prior Publication Data

US 2009/0099357 A1 Apr. 16, 2009

Related U.S. Application Data

(63) Continuation of application No. PCT/KR2006/001242, filed on Apr. 4, 2006.

(51) Int. Cl.
*A01N 43/90* (2006.01)
(52) U.S. Cl. .................................................. 514/262.1
(58) Field of Classification Search .................. None
See application file for complete search history.

(56) References Cited

U.S. PATENT DOCUMENTS 6,333,330 B1 12/2001 Bunnage et al.
2004/0029891 A1 2/2004 Ghazzi et al.

OTHER PUBLICATIONS

Program and Abstract for "10th Biennial Meeting of the Asia Pacific Society for Sexual Medicine", Oct. 4-8, 2005, cover and pp. 1, 10-12,, 32, 33.

*Primary Examiner* — Jeffrey Murray
(74) *Attorney, Agent, or Firm* — Lucas & Mercanti, LLP (57) ABSTRACT

The present invention relates to an agent for preventing and treating benign prostatic hyperplasia (BPH) and lower urinary tract symptoms (LUTS) associated with BPH and a relaxant for relaxing urethral smooth muscle or prostatic smooth muscle comprising a pyrazolopyrimidinone compound as an effective ingredient. The agent in accordance with the present invention can provide nitric oxides by inhibiting the activity of PDE-5 that decomposes c-GMP, and the provided nitric oxides relax the urethral smooth muscle or the prostatic smooth muscle to lower the intraurethral pressure (IUP), thus treating BPH and LUTS associated with BPH. Furthermore, the time required for reaching a maximum blood concentration is shorter and the half-life is longer than the other PDE-5 inhibitors, thus reducing the frequency of administration. Moreover, the agent of the invention causing few side effects can be efficiently used as a safe drug.

10 Claims, 4 Drawing Sheets

AGENT FOR THE PREVENTION AND TREATMENT OF PROSTATIC HYPERPLASIA COMPRISING PYRAZOLOPYRIMIDINONE COMPOUND

CROSS REFERENCE TO RELATED APPLICATIONS

This application is a continuation of PCT/KR2006/001242, filed Apr. 4, 2006, the disclosure of which is incorporated herein by reference.

TECHNICAL FIELD

The present invention relates to an agent for preventing and treating benign prostatic hyperplasia (BPH) and lower urinary tract symptoms (LUTS) associated with BPH and a relaxant for relaxing urethral smooth muscle or prostatic smooth muscle, both comprising a pyrazolopyrimidinone compound as an effective ingredient.

BACKGROUND ART

Prostate is a gland about the size of a walnut that is only present in men. It is located just below a urinary bladder and surrounds the urethra, the tube through which urine flows from the urinary bladder and out through the penis. The urethra passes diagonally through the front of prostate. The ejaculatory ducts on both sides of the prostate penetrate parenchyma behind the urethra. The parenchyma of the prostate is divided into three glandular lobes: middle lobe located above the ejaculatory ducts and side lobes in right and left of the urethra below the ducts. It is of tubulo-alveolar structure and is classified roughly into glandular tissue and interstitial tissue. The interstitial tissue consists of 30 to 50 small glandular lobes, from which prostatic ducts open chiefly into the prostatic sinuses that lie on either side of the seminal colliculus on the posterior wall of the prostatic urethra.

The prostate is one of the male accessory reproductive organs having a reproductive function along with testicles and seminal vesicles. It produces prostatic secretions of about one-third of seminal fluid. The prostatic secretions increase the mobility of sperms by nourishing the sperms produced in the testicles and also by preventing ejaculated semen from congealing, thus aiding the sperms mobility. Moreover, the prostatic secretions of alkaline act as an important vehicle for semen activity, i.e., they neutralize the strong acidic environment of female oviduct to help the sperms to be fertilized with an egg safely.

Benign prostatic hyperplasia (BPH) is a common disorder that affects older men aged above 50 years and is often associated with lower urinary tract symptoms (LUTS), thus deteriorating an individual's quality of life. The primary predisposing factors that spur the development of BPH are the aging and the presence of male hormones (androgens). Judging from the fact that men who have innate testicular insufficiency or whose testicles were removed are not affected with BPH, it can be understood that the male hormones participate in BPH as a predisposing factor. Besides, the differences of human species, environments, dietary lives, etc. may become the predisposing factors of BPH.

In general, the presence of histological BPH is in men aged 30 to 40 years, the incidence increases to the most men in aged above 60 years, and above 50% of enlarged prostates develop into those palpable with increasing ages [Prostate 1996 (suppl. 6) 67-73]. In is general, above 30% of tissue in the prostate have fibromuscular characteristics and it relates anatomically and functionally to the urinary bladder (Prostate 1981 2:35-49).

The symptoms of BPH include a hesitant, interrupted and weak stream; urgency and leaking or dribbling; and more frequent urination, especially at night. Since these symptoms develop slowly over the long haul, such symptoms may be considered simply as those caused by the aging process, which may develop in serious conditions such as hydronephrosis or uremia.

The diagnosis of BPH is carried out initially by identifying the degree of the symptoms and by palpation of the prostate through the rectum. For an accurate diagnosis, thorough examinations such as urodynamic studies, ultrasonography, etc., are referred to and treatment options are decided based on the results of such examinations.

Lower urinary tract symptoms (LUTS) may be caused by obstruction of the urinary tract due to an enlarged prostate consisting of epithelial cells and smooth muscles, reaction of the urinary bladder against the obstruction of the urinary tract, and strong contractions of smooth muscles due to stimuli of alpha-sympathetic nerves. Various symptoms related to processes of storing and voiding urine are collectively called lower urinary tract symptoms (LUTS). Storing difficulty symptoms include frequent urination, urgent urination, urgent incontinence, night urination (nycturia), painful urination (dysuria), etc. Voiding difficulty symptoms include hesitant urination, stress urination, weakened ureter, residual urine sense, urinary retention (anuresis), etc.

A variety of structural or medical conditions can cause LUTS, and it has been known that the predisposing factors of LUTS are bladder outlet obstruction, abnormalities in detrusor contraction, detrusor overactivity, etc., however, the primary factor is urethral obstruction by BPH. Accordingly, it has been considered that the treatment of the urethral obstruction lessens LUTS.

The treatments for BPH, the primary factor of LUTS, are classified roughly into surgery and drug therapies. The most available treatment for BPH was surgery even ten years before; whereas, drug therapies using alpha-receptor blockers, drugs for relaxing the smooth muscle that surround the prostate, and 5-alpha-reductase inhibitors, drugs for reducing the volume of the prostate, have been introduced recently. Moreover, with the development in the biomedical engineering field, newer methods capable of treating BPH, not dependent upon surgery, such as balloon dilatation, hyperthermia, laser therapy, transurethral needle ablation (TUNA), etc., have been developed and wide used.

Since it has been known that the alpha-receptors play an important role in the tension of smooth muscles in various tissues, their blockers have been applied to treatment of hypertension ahead of time. The typical alpha-receptor blocker is quinazolines such as alfuzocin, terazosin, doxazosin, prazosin, tamsulosin, etc. The alpha-blockers for relaxing the smooth muscle adjacent to the prostate are used for treatment of urethral obstruction and dysuria due to BPH. Such drugs can be used in the treatment of hypertension. Since such drugs may cause acute hypotension, sleepiness, dizziness, etc. for 30 to 120 minutes after administration, patients should administrate the drugs at night if possible and be careful when sitting down or sitting up in beds.

Since uroselective alpha-blockers like tamsulosin recently developed operate on contraction of the prostatic smooth muscle more selectively than existing alpha-blockers, they have advantages in that they cause few side effects comparatively and improve patient compliance. However, since the alpha-blockers direct expand the urethra to solve the dysuria, they also have drawbacks in that the treatment using such drugs returns to its initial state if stopping the drug administration. On the other hand, the 5-alpha-reductase inhibitors such as finasteride gradually reduce the volume of the prostate. That is, the 5-alpha-reductase inhibitors block dihydrotestosterone (DHT) that enlarges the prostate to reduce the volume of the enlarged prostate, thus increasing uroflow and relieving the dysuria in the long term. Besides, the 5-alpha-reductase inhibitors have advantages in that they can be administrated along with other drugs for hypertension, circulators, antibiotics, etc., since they have no interactions with other drugs. At the same time, the 5-alpha-reductase inhibitors have drawbacks in that patients should administrate the drugs over minimum six months steadily in order to improve related conditions, and they may cause side effects such as hyposexuality, impotence, decrease of ejaculate, etc.

One of the major factors of LUTS is that the alpha-receptors increase the tension of the smooth muscles in prostatic capsule and bladder neck by contraction and relaxation of the prostatic smooth muscle. Accordingly, the alpha-receptor blockers relax the tension of the prostatic smooth muscle to improve LUTS. However, such alpha-receptor blockers have no selectivity capable of distinguishing three types of al-receptors and have the same affinities as those al-receptors. As a result, they may be associated with side effects due to vasodilation, such as dizziness, asthenia, etc. (European Urology 2005 47:824-837).

Testosterone, one of the predisposing factors of BPH, is converted into 5-a-dihydrotestosterone via 5-a-reductase in the prostate. The 5-a-dihydrotestosterone affects the development and growth of the prostate. Accordingly, the 5-a-reductase inhibitors reduce the volume of the enlarged prostate by inhibiting testosterone from being converted into 5-a-dihydrotestosterone, thus providing desirable efficacies for LUTS (BJU International 2005 96:237-243, Clinical Therapeutics 2006 28:13-25). However, it has been known that the 5-a-reductase inhibitors reducing the volume of the prostate induce sexual dysfunctions (European Urology 2005 47:824-837).

Meanwhile, it has been reported recently that phosphodiesterase-5 (PDE-5) inhibitors, well known as effective ingredient for the treatment of male impotence, act on BPH and various conditions related to BPH (Urol clin North Am 2005 32:511-525; BJU Int 2002 90:836-839) which will now be described in detail hereinafter.

Functions of storing and expelling urine in the lower urinary tract depend on the nervous mechanism controlling various components of urethral outlet and activities of bladder. In general, the nervous system controls detrusor, urethral stump and external urethral sphincter to control uroflow (Journal of Urology 1995 153:2004-2009). Nitric oxide (NO) is a neurotransmitter, released from non-adrenergic, non-cholinergic nerves, which acts on urethral smooth muscle to facilitate the relaxation of urethra (Journal of Pharmacology 1998 357: 213-219).

Moreover, one of the conditions related to LUTS is endothelial dysfunction, which is called a state that endothelial-dependent vasodilatation is weakened due to the decrease in activity of nitric oxides. Nitric oxides produced by endothelial nitric oxide synthase (eNOS) activate guanylate cyclase. Activated guanylate cyclase induces the vasodilation, as a result of increasing c-GMP. Meanwhile, the decrease in activity of nitric oxides results from the degenerated antioxidation defense mechanism, manifestation or decreased activity of eNOS, and destruction by active oxygen. The nitric oxides, which are present in the prostate, control the prostatic smooth muscle and prevent the contraction of bladder that induces it hyperactivity, thus reducing LUTS (European Urology 2005 47:824-837). Accordingly, nitric oxide donors that relax the urethral smooth muscle and the prostatic smooth muscle can improve LUTS.

Sildenafil, one of the conventional PDE-5 inhibitors, inhibits the activity of PDE-5 that decomposes c-GMP to relax the prostatic smooth muscle via c-GMP route associated with nitric oxides (BJU International 2002 90:836-839).

The inventors of the present invention have disclosed WO2000/027848 (Corresponding Korean Patent No. 0353014), in which a novel pyrazolopyrimidinone compound is prepared to have efficacy on inhibition of PDE-5. Then, the inventors of the present invention have continued to study on the pyrazolopyrimidinone compound, one of the PDE-5 inhibitors, and confirmed that the pyrazolopyrimidinone compound shows more excellent efficacy on benign prostatic hyperplasia (BPH) and lower urinary tract symptoms (LUTS) associated with BPH than the conventional sildenafil. Moreover, the inventors of the present invention have verified that since the pyrazolopyrimidinone compound has an in vivo half-life longer than the other PDR-5 inhibitors, the administration convenience is increased and the time required for reaching a maximum blood concentration is shortened; and since the pyrazolopyrimidinone compound is less affected by the liver metabolism as compared with the other drugs, the possibility of side effects by interactions between drugs is very low (Xenbbiotica 2004 34:973-982) and completed the present invention.

SUMMARY OF THE INVENTION

Accordingly, an object of the present invention is to provide an agent for preventing and treating benign prostatic hyperplasia (BPH) comprising a pyrazolopyrimidinone compound expressed as formula 1 as an effective ingredient.

Another object of the present invention is to provide an agent for preventing and treating lower urinary tract symptoms (LUTS) comprising a pyrazolopyrimidinone compound expressed as formula 1 as an effective ingredient.

A yet another object of the present invention is to provide a relaxant for relaxing urethral smooth muscle or prostatic smooth muscle comprising a pyrazolopyrimidinone compound expressed as formula 1 as an effective ingredient.

To accomplish the above technical object, the present invention provides an agent for preventing and treating benign prostatic hyperplasia (BPH) comprising a pyrazolopyrimidinone compound as an effective ingredient.

Moreover, the present invention provides an agent for preventing and treating lower urinary tract symptoms (LUTS) comprising a pyrazolopyrimidinone compound as an effective ingredient.

Furthermore, the present invention provides a relaxant for relaxing urethral smooth muscle or prostatic smooth muscle.

According to the present invention, the agent comprising the pyrazolopyrimidinone compound of formula 1 can relax urethral smooth muscle or prostate smooth muscle by inhibiting the activity of PDE-5 that decomposes c-GMP (Nippon Hinyokika Gakkai Zasshi 1994 85:1124-1130; J Urol 1995 153:2004-2009; Eur J Pharmacol 1998 357:213-219), and improve the lower urinary tract symptoms (LUTS) caused by the benign prostatic hyperplasia (BPH) by lowering intraurethral pressure. Moreover, the pyrazolopyrimidinone compound of formula 1 in accordance with the present invention has an in vivo half-life longer three times than the other drugs of the same mechanism in comparison with the other PDE-5 inhibitors. Accordingly, it has various advantages in that it is possible to reduce the number of time of administration, the time required for reaching a maximum blood concentration is shortened, and the frequency of occurrence of side effects is very low. Furthermore, since the pyrazolopyrimidinone compound of formula 1 in accordance with the present invention is less affected by the liver metabolism as compared with the other drugs, differently from the existing drugs metabolized through cytochrome P450 3A4, the possibility of side effects by interactions between drugs is very low (Xenobiotica 2004 34:973-982), and it has a larger margin of safety than the other PDE-5 inhibitors.

DESCRIPTION OF DRAWINGS

The above and other features of the present invention will be described with reference to certain exemplary embodiments thereof illustrated the attached drawings in which.

Figure 1:
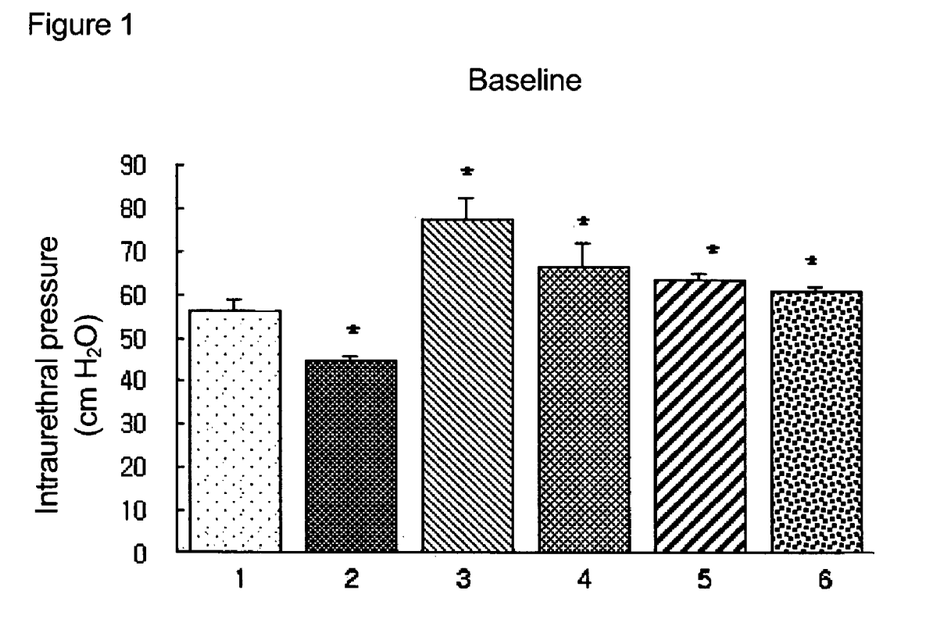
FIGS. 1 to 4 are graphs showing the decreases of intraurethral pressure measured varying electric stimulations in benign prostatic hyperplasia (BPH) models, after repeated administrations of the pyrazolopyrimidinone compound in accordance with the present invention.
Figure 2:
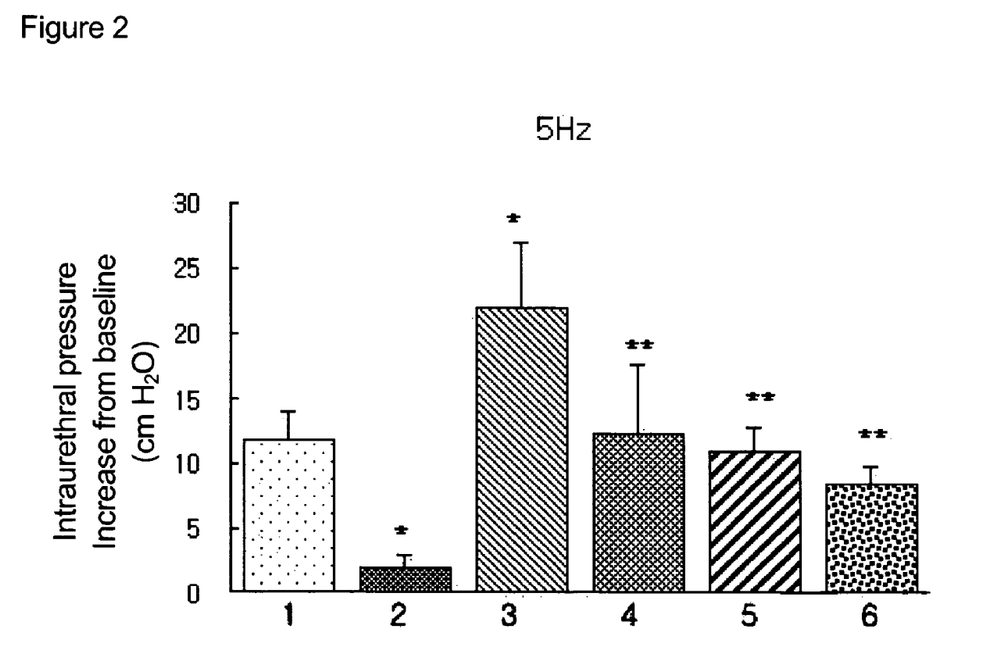
Figure 3:
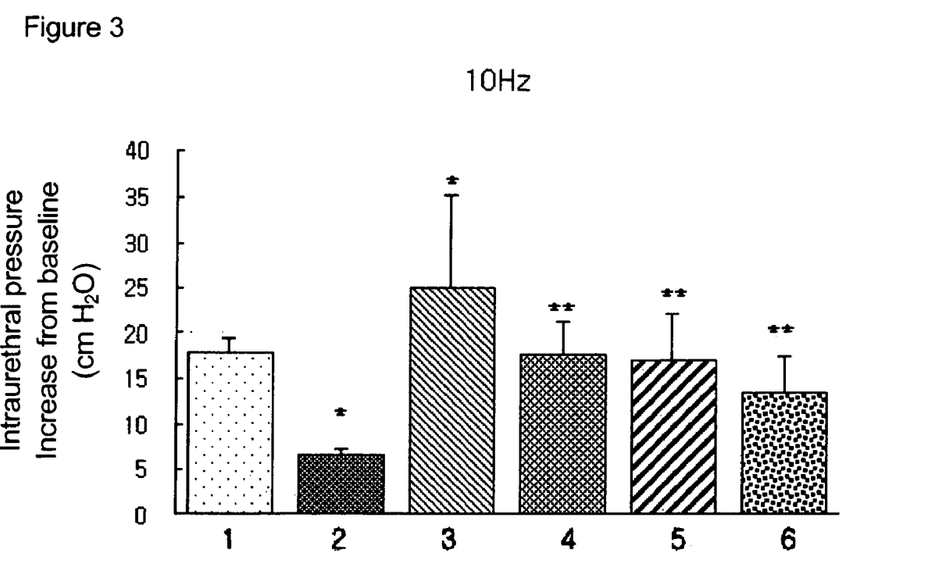
Figure 4:
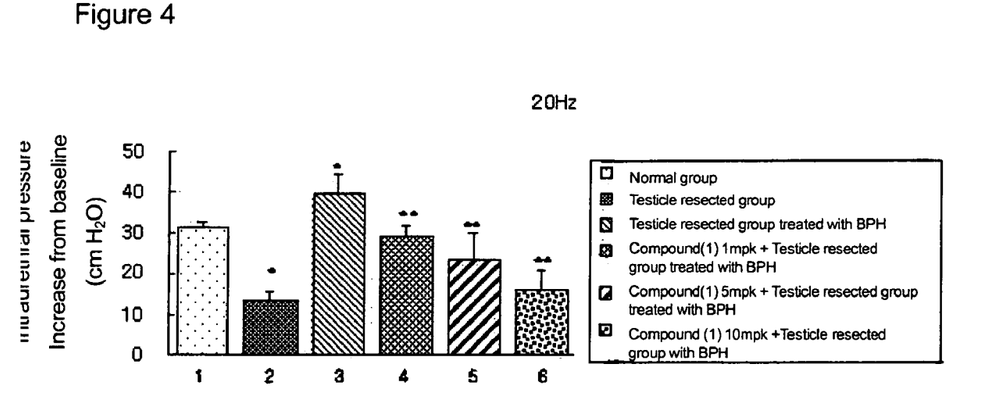
Figure 5:
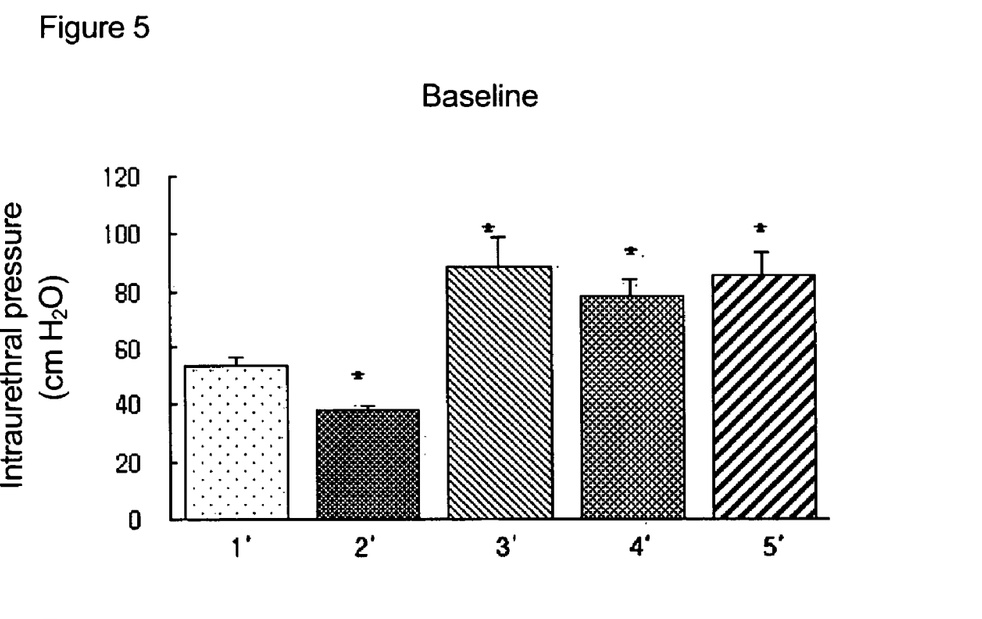
FIGS. 5 to 8 are graphs showing the decreases of intraurethral pressure measured varying electric stimulations in benign prostatic hyperplasia (BPH) models, after single administrations of the pyrazolopyrimidinone compound in accordance with the present invention.
Figure 6:
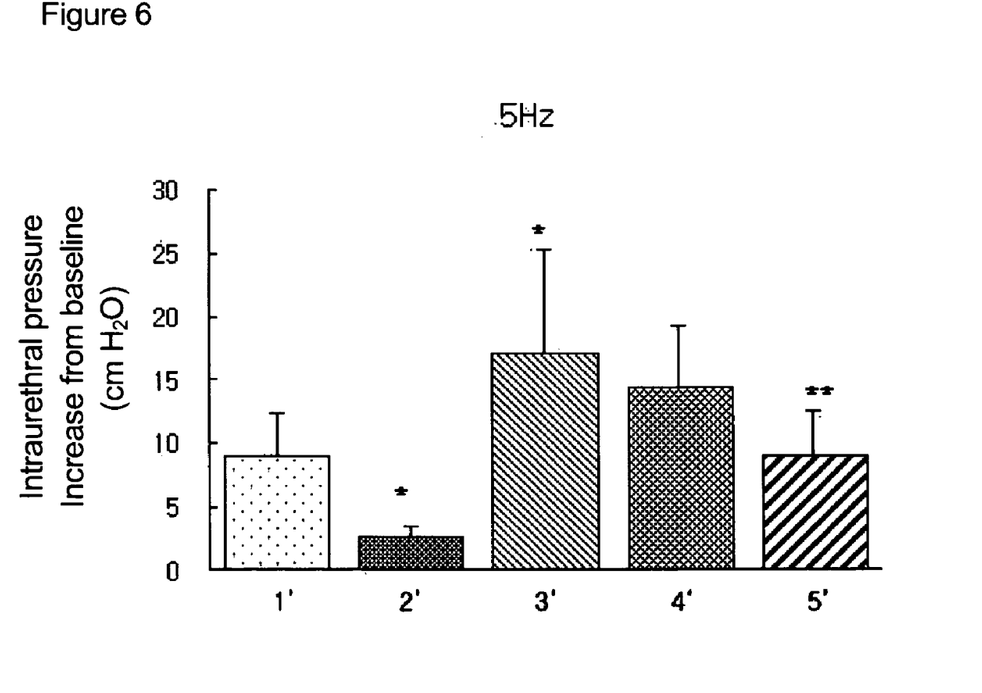
Figure 7:
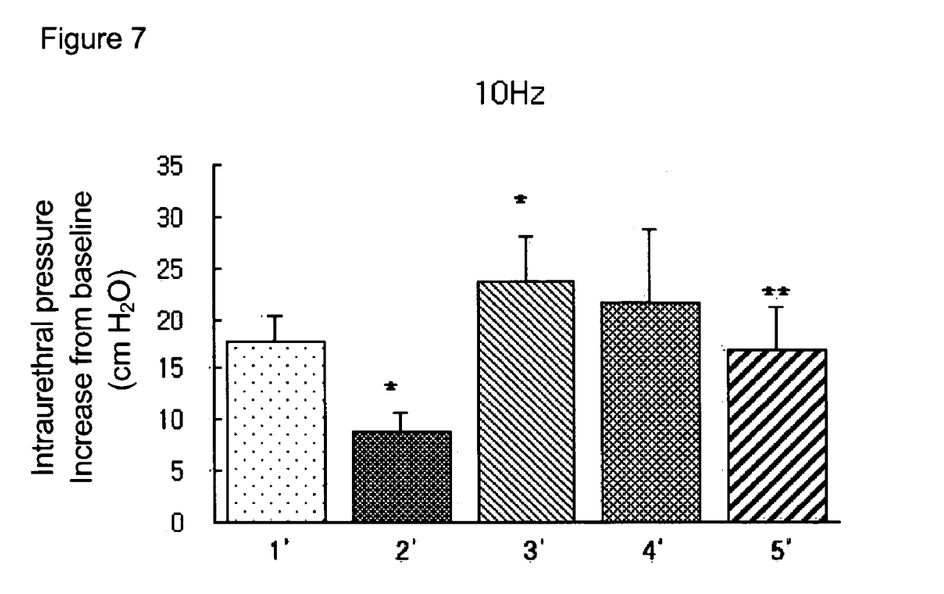
Figure 8:
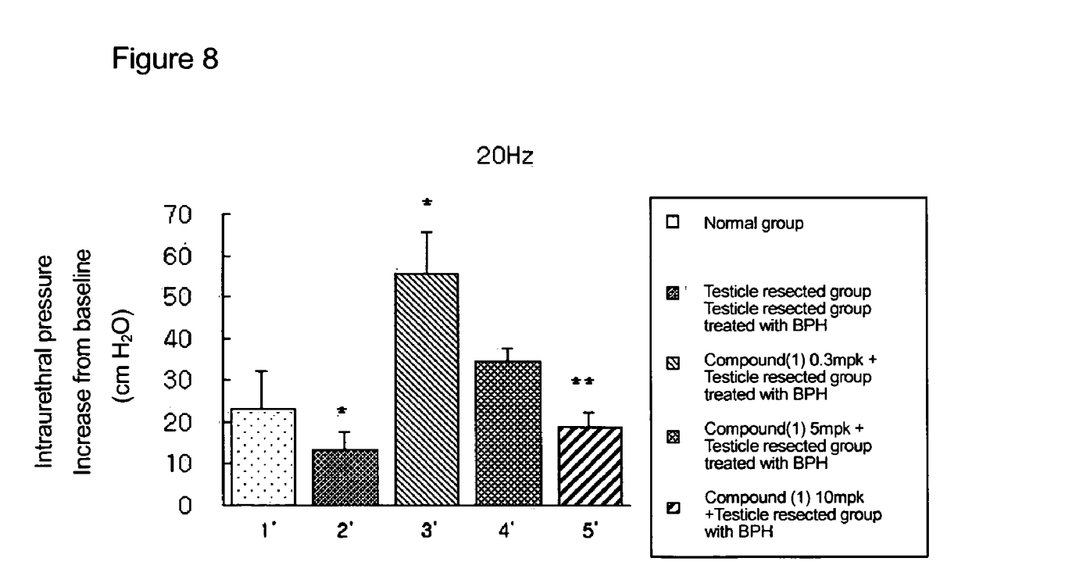

DESCRIPTION OF MAJOR SYMBOLS IN THE ABOVE FIGURES

*: Shown significant differences compared with normal rats
**: Shown significant differences compared with BPH control groups
1 and 1': Normal groups
2 and 2': Testicle resected groups
3 and 3': Testicle resected groups treated with solvent
4: Testicle resected group treated with 1 mpk(mg/kg) of the compound of formula 1 in accordance with the present invention
4': Testicle resected group treated with 0.3 mpk(mg/kg) of the compound of formula 1 in accordance with the present invention
5: Testicle resected group treated with 5 mpk(mg/kg) of the compound of formula 1 in accordance with the present invention
5': Testicle resected group treated with 1 mpk(mg/kg) of the compound of formula 1 in accordance with the present invention
6: Testicle resected group treated with 10 mpk(mg/kg) of the compound of formula 1 in accordance with the present invention

DETAILED DESCRIPTION OF THE INVENTION

The present invention provides an agent comprising a pyrazolopyrimidinone compound (5-[2-propyloxy-5-(1-methyl-2-pyrrolidinylethylamidosulfonyl)phenyl]-1-methyl-propyl-1,6-dihydro-7H-pyrazolo(4,3-d)pyrimidin-7-one) expressed as formula 1 as an effective ingredient for preventing and treating benign prostatic hyperplasia (BPH).

Formula 1

The pyrazolopyrimidinone compound represented as formula 1 is one of the PDE-5 inhibitors and has characteristics in that it has a strong inhibitive activity and an excellent selectivity for PDE-5; it is readily absorbed as its solubility is improved; it has a good bioavailability and a large volume of distribution; and it has an in vivo half-life longer three times than sildenafil or vardenafil, a drug of the same mechanism.

Physicochemical properties of the pyrazolopyrimidinone compound of formula 1 are as follows: it is hardly dissolved in water; however, it is readily dissolved in acetic acid, methanol, chloroform and the like; and it is a white or pale yellow powder, not a hydrate or a solvate, having a melting point of 158 to 161° C., and having pKa1 and pKa2 of about 6.5 and 12.5, respectively.

The pyrazolopyrimidinone compound represented as formula 1 is prepared via a synthetic process consisting of roughly three steps. The inventors of the present invention have disclosed a method for preparing the same in WO2000/027847 (Corresponding Korean Patent No. 0353014), which will now be described roughly as follows.

First, in the first step, 4-[2-propyloxy-5-(chlorosulfonyl)benzamido]-1-methyl-3-propyl-5-carbamoyl pyrazole is prepared. For such preparation, a specified amount of 4-[2-propyloxybenzamido]-1-methyl-3-propyl-5-carbamoyl pyrazole is added to a specified amount of chlorosulfonic acid cooled to 0° C., then, the resultant mixture is stirred, filtered, washed and dried to obtain 4-[2-propyloxy-5-(chlorosulfonyl)benzamido]-1-methyl-3-propyl-5-carbomoyl pyrazole.

In the second step, from the pyrazole compound prepared in the first step, 4-[2 propyloxy-5-(1-methyl-2-pyrrolidinylethylamidosulfonyl)benzamido]-1-methyl-3-propyl-5-carbomoyl pyrazole is prepared. For such preparation, a specified amount of 2-(2-aminoethyl)-1-methylpyrrolidine is added in dichloromethane solution of the specified amount of 4-[2-propyloxy-5-(chlorosulfonyl)benzamido]-1-methyl-3-propyl-5-carbamoyl pyrazole prepared in the first step to be stirred. Then, the reactant solution is diluted with dichloromethane. The organic layer is washed, dried, concentrated and filtered to obtain 4-[2-propyloxy-5-(1-methyl-2-pyrrolidinylethylamidosulfonyl)benzamido]-1-methyl-3-propyl-5-carbomoyl pyrazole is obtained.

Last, in the third step, the pyrazolopyrimidinone compound of the present invention (5-[2-propyloxy-5-(1-methyl-2-pyrrolidinylethylamidosulfonyl)phenyl]-1-methyl-propyl-1,6-dihydro-7H-pyrazolo(4,3-d)pyrimidin-7-one) is prepared from the compound obtained in the second step. For such preparation, the specified amount of pyrazole compound prepared in the second step is dissolved in t-butanol. A specified amount of potassium t-butoxide is added in the resultant solution and, then, reflux-stirred for a predetermined time. After the resultant solution is cooled, diluted, washed and dried, distillation under reduced pressure, solvolysis and silica gel column chromatography are carried out, thus obtaining a specified amount of pure pyrazolopyrimidinone compound of the present invention.

The present invention relates to an agent for preventing and treating benign prostatic hyperplasia (BPH) and lower urinary tract symptoms (LUTS) related to BPH and a relaxant for relaxing urethral smooth muscle or prostatic smooth muscle comprising a pyrazolopyrimidinone compound as an effective ingredient, which can be described as follows.

The present invention provides 1) a relaxant for relaxing urethral smooth muscle or prostatic smooth muscle, which constitutes urethra or the prostate; 2) an agent for preventing and treating benign prostatic hyperplasia (BPH) by relaxing the urethral smooth muscle or the prostatic smooth muscle via the relaxant; and, further, 3) a relaxant and an agent comprising a pyrazolopyrimidinone compound as an effective ingredient suitable for preventing and treating lower urinary tract symptoms (LUTS) associated with BPH.

More particularly, the present invention is directed to provide an agent for preventing and treating benign prostatic hyperplasia (BPH) comprising a pyrazolopyrimidinone compound as an effective ingredient.

In addition, the present invention provides an agent for preventing and treating lower urinary tract symptoms (LUTS) comprising the pyrazolopyrimidinone compound as an effective ingredient.

The agent comprising the pyrazolopyrimidinone compound as an effective ingredient for preventing and treating BPH or LUTS in accordance with the present invention inhibits the activity of PDE-5.

The agent comprising the pyrazolopyrimidinone compound as an effective ingredient for preventing and treating BPH or LUTS in accordance with the present invention does not inhibit the activity of PDE-11 but inhibits the activity of PDE 5.

The agent comprising the pyrazolopyrimidinone compound as an effective ingredient for preventing and treating BPH or LUTS in accordance with the present invention does not cause testicle toxicity or myalgia, since it does not have an inhibiting powder for the activity of PDE-11.

The agent comprising the pyrazolopyrimidinone compound as an effective ingredient for preventing and treating BPH or LUTS in accordance with the present invention lowers intraurethral pressure.

The effect of the agent comprising the pyrazolopyrimidinone compound as an effective ingredient for preventing and treating BPH or LUTS in accordance with the present invention continues for 12 to 24 hours without accumulation of drug with an administration frequency of one time.

The agent comprising the pyrazolopyrimidinone compound as an effective ingredient for preventing and treating BPH or LUTS in accordance with the present invention reaches a maximum blood concentration within 50 to 70 minutes, preferably 60 minutes.

The half-life of the agent comprising the pyrazolopyrimidinone compound as an effective ingredient for preventing and treating BPH or LUTS in accordance with the present invention is 9 to 15 hours.

Furthermore, the present invention provides a relaxant comprising the pyrazolopyrimidinone compound as an effective ingredient for relaxing urethral smooth muscle or prostatic smooth muscle.

The relaxant comprising the pyrazolopyrimidinone compound as an effective ingredient for relaxing urethral smooth muscle or prostatic smooth muscle in accordance with the present invention inhibits the activity of PDE-5.

The relaxant comprising the pyrazolopyrimidinone compound as an effective ingredient for relaxing urethral smooth muscle or prostatic smooth muscle in accordance with the present invention inhibits the activity of PDE-5, not PDE-11 activities.

The relaxant comprising the pyrazolopyrimidinone compound as an effective ingredient for relaxing urethral smooth muscle or prostatic smooth muscle in accordance with the present invention does not cause testicle toxicity or myalgia, since it does not have an inhibiting power for the activity of PDE-11.

The relaxant comprising the pyrazolopyrimidinone compound as an effective ingredient for relaxing urethral smooth muscle or prostatic smooth muscle in accordance with the present invention lowers intraurethral pressure.

The effect of the relaxant comprising the pyrazolopyrimidinone compound as an effective ingredient for relaxing urethral smooth muscle or prostatic smooth muscle in accordance with the present invention continues for a long time with a low administration frequency.

The effect of relaxant comprising the pyrazolopyrimidinone compound as an effective ingredient for relaxing urethral smooth muscle or prostatic smooth muscle in accordance with the present invention continues for 12 to 24 hours without accumulation of drug with an administration frequency of one time.

The relaxant comprising the pyrazolopyrimidinone compound as an effective ingredient for relaxing urethral smooth muscle or prostatic smooth muscle in accordance with the present invention reaches a maximum blood concentration within 50 to 70 minutes, preferably 60 minutes.

The half-life of the relaxant comprising the pyrazolopyrimidinone compound as an effective ingredient for relaxing urethral smooth muscle or prostatic smooth muscle in accordance with the present invention is 9 to 15 hours.

Hereinafter, the present invention will now be described in detail.

When prostatic tissue surrounding the urethra is enlarged abnormally, intraurethral pressure is increased to cause benign prostatic hyperplasia (BPH associated with dysuria. Such BPH may result in lower urinary tract symptoms (LUTS). Various symptoms related to processes of storing and voiding urine are collectively called lower urinary tract symptoms (LUTS). The storing difficulty symptoms include frequent urination, urgent urination, urgent incontinence, night urination (nycturia), painful urination (dysuria), etc. The voiding difficulty symptoms include hesitant urination, stress urination, weakened ureter, residual urine sense, urinary retention (anuresis), etc. A variety of structural or medical conditions can cause LUTS, and it has been known that the predisposing factors of LUTS are bladder outlet obstruction, abnormalities in detrusor contraction, detrusor overactivity, etc., however, the primary factor is urethral obstruction by BPH. Accordingly, it has been considered that the treatment of the urethral obstruction lessens LUTS.

The treatments for such conditions are classified roughly into surgery and drug therapies. The surgery is the ultimate step and the drug therapies have attracted attention recently. A typical drug for treating the conditions of BPH is an alpha-blocker, which acts on urethral or prostatic smooth muscle to relax the smooth muscle, thus treating the urethral obstruction and dysuria due the BPH. Accordingly, the drug for improving the relaxation of urethral smooth muscle can contribute to the prevention and treatment of BPH and LUTS.

Meanwhile, various researches on the treatment of BPH have reported that PDE-5 inhibitors, well known as effective ingredient of the treatment of male impotence, have efficacies on BPH and LUTS associated with BPH.

That is, in physiological functions of lower urinary tract, nitric oxides (NOs) control the relaxation and contraction of the prostatic smooth muscle and the urethral smooth muscle to reduce BPH and LUTS associated with BPH (Nippon Hinyokika Gakkai Zasshi 1994 85:1124-1130; J Urol 1995 153:2004-2009; Eur J Pharmacol 1998 357:213-219).

Moreover, nitric oxides produced by endothelial nitric oxide synthase (eNOS) activate guanylate cyclase. The guanylate increases c-GMP to relax the urethral smooth muscle. Meanwhile, when the activity of nitric oxides that control the prostatic smooth muscle and inhibit the bladder contraction is decreased, the nitric oxide-dependent prostatic smooth muscle relaxation is weakened. (European Urology 2005 47:824-837). Accordingly, nitric oxide donors that relax the urethral smooth muscle and the prostatic smooth muscle can improve LUTS, thus being applied efficiently to the treatment of BPH consequently.

Furthermore, since it was known that zaprinast, one of the non-specific PDE-5 inhibitors that have NO-cGMP route as a mechanism, relaxed urethral smooth muscle of a rabbit, there have been reported various researches on applicability of the PDE-5 inhibitors including the compound of formula 1 in accordance with the present invention to BPH (Eur J Pharmacol 11994 266:269-275). Actually, it has been reported that Viagra improves the lower urinary tract symptoms (LUTS) caused by the benign prostatic hyperplasia (BPH) as a result of clinical trials, which results from the prostatic smooth muscle's relaxation action associated with the NO-cGMP route. More recently, it has been reported that Clalis, one of the drugs for treating impotence, has the efficacy on improvement of the lower urinary tract symptoms (LUTS) caused by the benign prostatic hyperplasia (BPH) as a result of phase 2 clinical trials (BJU Int 2003 90:836 839; BJU Int 2003 92:534-538; http://www.ICOS.com).

In the clinical trials of Viagra, having administrated sildenafils to 300 patients for 12 weeks, it has been found that improvements of impotence, self confidence and quality of life as well as irritative and obstructive LUTS are increased noticeably. Moreover, in domestic clinical trails, after administrating such drugs to 68 patients for 12 weeks, it has been found that the lower urinary tract symptoms (LUTS) are reduced from 15.3 points to 12.3 points on the basis of the International Prostate Symptom Score (IPSS) and the improvements on the impotence rise from an average point of 27.4 to that of 41.5 on the basis of the International Index of Erectile Function (IIEF) (http:medscape.com/viewarticle/517500, Financial News 224.11.11). ICOS corporation has reported that, in double-blind, placebo-controlled and POC phase 2 clinical trials, having administrating 5 mg of Clalis once a day for 6 weeks, the IPSS rises 2.8 points (1.2 points rises in placebo-controlled group), and in case of increasing a dose to 20 mg and administrating such drugs for additional 6 weeks, the IPSS rises 3.8 points (1.7 points rises in placebo-controlled group), the two doses all having statistical significance. Meanwhile, their side effects were dyspepsia, back pain, headache, etc. and the interrupt rate of administration due to the side effects was 3.6% (1.4% in placebo-controlled group) (http://www.ICOS.com).

As described above, considering that the relaxations of the urethral smooth muscle and the prostatic smooth muscle and the treatments of LUTS and BPH are associated closely with each other, we, the inventors of the present invention have judged that the agent comprising the pyrazolopyrimidinone compound as an effective ingredient of the present invention inhibits PDE-5 that decomposes c-GMP to relax the urethral smooth muscle and the prostatic smooth muscle via the c-GMP route associated with the nitric oxides, thus efficiently improving the benign prostatic hyperplasia (BPH) and the lower urinary tract symptoms (LUTS) caused by BPH, and carried out various experiments. That is, we have observed that the compound of the invention significantly inhibits intraurethral pressure caused by BPH. Moreover, we have confirmed that, in repeated or single administrations in rat models having enlarged prostates, the increases in the intraurethral pressure are significantly inhibited dose-dependently and statistically (See FIGS. 1 to 8). Furthermore, we have confirmed that the compound of the invention relaxes the urethral smooth muscle and the prostatic smooth muscle.

In addition, the present invention comprising the pyrazolopyrimidinone compound of formula 1 as an effective ingredient provides an excellent and stable agent, in view of pharmacokinetics, for preventing and treating benign prostatic hyperplasia (BPH) and lower urinary tract symptoms (LUTS) associated with BPH as compared with the other conventional PDE-5 inhibitors.

Practically, it has been found that the pyrazolopyrimidinone compound of formula 1 in accordance with the present invention has a high tissue affinity in the organs of genitourinary system as compared with the other conventional PDE-5 inhibitors, and its concentration is kept steadily in the related organs, differently from the other PDE-5 inhibitors, of which concentrations are rapidly decreased as time goes by (See Table 2).

Meanwhile, in the process of developing the pyrazolopyrimidinone compound of formula 1 in accordance with the present invention as an agent for treating impotence, a phase 1 clinical trial for assessing the safety, tolerability and pharmacokinetic/pharmacodynamic characteristics of the compound of formula 1 was carried out with healthy adults in Korea patients from August, 2001 to August, 2002, and such clinical trial was performed in England from April, 2002 to December, 2002 for overseas developments. As a result of such trials, the compound of formula 1 of the present invention was readily absorbed at 1 to 2 hours of $T_{max}$ after oral administration and the half-life was about 9 to 15 hours regardless of the doses administrated. Besides, after repeated administration once a day for 7 days, the noticeable accumulation of drug was not observed, from which it can be learned that the duration of the drug effect continues for 12 to 24 hours and, which was actually confirmed in a phase 3 clinical trial.

In addition, as a result of examination on abnormal responses to the test substance, no serious abnormal responses to the compound of formula 1 was found in a phase 1 clinical trial, and the majority was temporarily light cases. Moreover, in view of the patterns of side effects obtained in phase 2 and phase 3 clinical trials, the degree and frequency of the side effects were very lower than those of the existing oral agents for the treatment of impotence.

As indicated by Table 1 below, the compound of formula 1 in accordance with the present invention showed the most low administration interrupt rate among the PDE-5 inhibitors. Besides, the Clalis that has been most recently developed has possible side effects such as testicle toxicity or myalgia, since it inhibits the activity of PDE-11, whereas, since the compound of formula 1 in accordance with the present invention does not have an inhibiting power for the activity of PDE-11, such side effects were not manifested.

Furthermore, the residual rate of the compound of formula 1 in accordance with the present invention after liver metabolism was 93.0%, which was very higher than 34.6% of sildenafil, one of the conventional PDE-5 inhibitors, from which it can be understood that the compound of formula 1 of the invention has a very low possibility of side effects by interactions between drugs, since it is not affected by the liver metabolism as compared with the other drugs (Xenobiotica 2004 34:973-982).

TABLE 1

Interrupt rate (%) of administration due to side effects of PDE-5 inhibitors after clinical trials on impotence:

|  | Placebo | 5 mg | 10 mg | 20 mg | 25 mg | 50 mg | 100 mg | 200 mg |
|---|---|---|---|---|---|---|---|---|
| Viagra | 0.7 | — | — | — | 0.0 | 0.7 | 3.9 | — |
| Levitra | 1.6 | 2.7 | 2.9 | 6.6 | — | — | — | — |
| Cialis | 1.3 | 0.7 | 1.6 | 3.1 | — | — | — | — |
| Compound of Formula 1 | 0.0 | — | — | — | — | — | 0.0 | 1.2 | wherein, "-" denotes that no clinical trials are carried out.

Such results show that the compound of formula 1 in accordance with the present invention has less side effects and excellent pharmacokinetic characteristics as compared with the conventional drugs such as Viagra, Clalis, etc., thus enhancing the safety and the drug effect duration. Such enhanced safety and pharmacokinetic characteristics are identically applicable to the treatment of BPH and LUTS as well as impotence. As a result, since the compound of formula 1 in accordance with the present invention shows the same effects even once a day administration, it is a more convenient drug for administration and causes fewer side effects as compared with the conventional drugs administrated three times a day. Consequently, it can be learned that the compound of formula 1 in accordance with the present invention is a safe and effective agent for preventing and treating the benign prostatic hyperplasia (BPH) and the lower urinary tract symptoms (LUTS) associated with BPH or a relaxant for relaxing urethral smooth muscle or prostatic smooth muscle.

Accordingly, the pyrazolopyrimidinone compound of formula 1 in accordance with the present invention can be used effectively and safely as an agent for preventing and treating the benign prostatic hyperplasia (BPH) and lower urinary tract symptoms (LUTS) associated with BPH or a relaxant for relaxing the urethral smooth muscle or the prostatic smooth muscle.

The preventing and treating agent comprising the pyrazolopyrimidinone compound of formula 1 in accordance with the present invention may be used in the forms of general pharmaceutical formulation. That is, the pyrazolopyrimidinone compound of the invention may be used in various methods such as oral and parenteral administrations in actual clinical trials, and the oral administration is preferable in the present invention. Moreover, the pyrazolopyrimidinone compound of the invention may be formulated into various dosage forms using commonly used diluents or excipients such as fillers, expanders, bonding agents, humectants, disintegrants, surfactants, etc.

Solid dosages for oral administration include tablets, pillets, powders, granules, capsules, etc. Such solid dosages are prepared by admixing the pyrazolopyrimidinone compound of formula 1 with at least one excipient, such as starch, calcium carbonate, sucrose or lactose, gelatin, etc. In addition to simple expedients, lubricants such as magnesium styrate, talc, etc. may be added.

Liquid dosage forms for oral administration, such as suspensions, internal solutions, emulsions, syrups, etc., may comprise simple diluents, e.g., water and liquid paraffin, as well as various excipients, e.g., humectants, sweeteners, aromatics, preservatives, etc. Dosage forms for parenteral administration include sterilized aqueous solutions, non-aqueous solvents, suspensions, emulsions, lyophilized agents, suppositories, etc. Non-aqueous solvents and suspensions may be prepared using vegetable oils, such as propylene glycol and polyethylene glycol, olive oil, or using injectable esters such as ethyl oleate. As bases for suppositories, witepsol, macrogol, Tween 61, cacao oil, laurinic acid, and glycerogelatine are useful.

The dosages of pharmaceutical composition comprising the pyrazolopyrimidinone compound of formula 1 in accordance with the present invention may be varied according to various relevant factors, such as weight, age, sex, health status, diet and excretion rate of patients, time and method of administration, and severity of symptoms. In general, it is preferable to administrate such drugs in a total dosage of 20 to 200 mg once or several times a day to adults.

MODE FOR INVENTION

Hereinafter, the present invention will now be described more fully with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Example 1

Measurement of Effects on Repeated Administration of the Pyrazolopyrimidinone Compound of Formula 1 for the Increases of Intraurethral Pressure in BPH Rat Models The following experiment was carried out in order to measure the effects on the decreases of intraurethral pressure (IUP) via repeated administration of pyrazolopyrimidinone compound of formula 1 in accordance with the present invention.

In the present experiment, thirty-six male white Wistar rats of 300 to 350 g were randomly divided into six control groups of six rats. The first group (1) was left untreated as a normal control group and the other groups were those whose testicles were insected. From a couple of days after the operations, each rat in the third to sixth groups was given a daily hypodermic injection of 1 mg of testosterone and 0.01 mg of 17 beta-estradiol for 8 weeks. The second group (2) was those whose testicles were insected only; the third group (3) was treated with a solvent; the fourth group (4) was treated with 1 mg/kg of the pyrazolopyrimidinone compound of formula 1; the fifth group (5) was treated with 5 mg/kg of the pyrazolopyrimidinone compound of formula 1; and the sixth group (6) was treated with 20 mg/kg of the pyrazolopyrimidinone compound of formula 1, the fourth to sixth groups being orally administrated for 8 weeks. After 8 weeks, all rats were anesthetized by an intraperitoneal injection with 50 mg/kg of pentobarbital, and intubated with polyethylene needles. Saline solutions were perfused at a rate of 0.5 ml/10 min using syringe pumps to measure intraurethral pressures (IUP). In the measurement, 5, 10 and 20 Hz of electrostimulations were applied to hypogastric nerves using a stainless steel anode electrode, and the measured results were shown in FIGS. 1 to 4.

As shown in those figures, the baseline of the control group (2) whose testicles were resected was shown as lower than the normal control group (1), whereas, those in BPH models (3 to 6) were shown as higher than the control group (1). As a result, it could be identified that the intraurethral pressures were increased by the benign prostatic hyperplasia (BPH). Besides, it could be confirmed that the intraurethral pressures were decreased dose-dependently and significantly for the respective stimulations by the administrated pyrazolopyrimidinone compounds of formula 1 in the control groups (4 to 6). As a result, it could be understood that the agent comprising the pyrazolopyrimidinone compound of formula 1 in accordance with the present invention was usefully applicable to the prevention and treatment of the benign prostatic hyperplasia (BPH) and the lower urinary tract symptoms (LUTS) associated with BPH.

Example 2

Measurement of Effects on Single Administration of the Pyrazolopyrimidinone Compound of Formula 1 for the Increases of Intraurethral Pressure in BPH Rat Models The following experiment was carried out in order to measure the effects on the decreases of intraurethral pressure (IUP) via single administration of pyrazolopyrimidinone compound of formula 1 in accordance with the present invention.

In the present experiment, thirty male white Wistat rats of 300 to 350 g were randomly divided into five control groups of six rats. The first group (1') was left untreated as a normal group and the other groups were those whose testicles were resected. From a couple of days after the operations, each rat in the third to fifth groups was given a daily hypodermic injection of 1 mg of testosterone and 0.01 mg of 17 beta-estradiol for 8 weeks. After 8 weeks, all rats were anesthetized by an intraperitoneal injection with 50 mg/kg of pentobarbital, and intubated with polyethylene needles. The second group (2') was those whose testicles were resected only; the third group (3') was treated with a solvent; the fourth group (4') was treated with 0.3 mg/kg of the pyrazolopyrimidinone compound of formula 1; and the fifth group (5') was treated with 1 mg/kg of the pyrazolopyrimidinone compound of formula 1, the fourth and fifth groups being administrated via intravenous injections. Then, saline solutions were perfused at a rate of 0.5 ml/10 min using syringe pumps to measure intraurethral pressures (IUP). In the measurement, 5, 10 and 20 Hz of electrostimulations were applied to hypogastric nerves using a stainless steel anode electrode, and the measured results were shown in FIGS. 5 to 8.

As shown in those figures, the baseline of the control group (2') whose testicles were resected only was shown as lower than the normal group (1'), whereas, those in BPH models (3' to 5') were shown as higher than the control group (1') in the same results as FIGS. 1 to 4. As a result, it could be identified that the intraurethral pressures were increased by the benign prostatic hyperplasia (BPH). Besides, it could be confirmed that the increases in the intraurethral pressure were prevented dose-dependently when administrating the pyrazolopyrimidinone compounds of formula 1 to the rats in the control groups (4' to 5'). Although the control group (4') treated with 0.3 mg/kg of the pyrazolopyrimidinone compound of formula 1 did not show significant decreases at 5 and 10 Hz, it showed a significant increase at 20 Hz. Moreover, it could be confirmed that the agent comprising the pyrazolopyrimidinone compound of formula 1 in accordance with the present invention provided excellent effects on the prevention of increases in the intraurethral pressure, in comparison with the sildenafil of same volume, one of the PDE-5 inhibitors. As a results it could be understood that the agent comprising the pyrazolopyrimidinone compound of formula 1 in accordance with the present invention was usefully applicable to the prevention and treatment of the benign prostatic hyperplasia (BPH) and the lower urinary tract symptoms (LUTS) associated with BPH.

Example 3

Tissue Distribution in Urogenital Organs

The following experiment was carried out in order to assess the distribution in urogenital organs via administration of pyrazolopyrimidinone compound of formula 1 in accordance with the present invention.

Male white Sprague-Dawley (SD) rats were randomly assigned by four to five rats at different time points. Each 30 mg/kg/5 ml of the pyrazolopyrimidinone compound of formula 1 and sildenafil were dissolved in 0.05 N citric acid and administrated. At different time points of 30 minutes, 2 hours and 6 hours after administration, bloods were collected through abdominal aortas and urogenital organs were extracted. Phosphate buffer of pH 7.4 was added to the extracted organs to be homogenized. Then, the homogenized organs were centrifuged to quantify the contents of the pyrazolopyrimidinone compound of formula 1 and sildenafil in the supernatants using high performance liquid chromatography (HPLC). Analyses were performed using a Hichrom HIRPB column (150×4.6 mm, particle size: 5 μm) at fixed wavelength of 292 nm with a mobile phase mixed with 20 nM of $KH_2PO_4$ and acetonitrile in a volume ratio of 70:30. The mobile phase flow rate was 1 ml/min. and the amount of sample introduced was 100 ml. The pyrazolopyrimidinone compound of formula 1 and sildenafil were quantified as internal standard and area ratio.

TABLE 2

| | Concentration in organs (mcg/ml) | |
| --- | --- | --- |
| Time (min) | Compound of formula 1 | Sildenafil |
| 30 | 0.386 | 0.319 |
| 120 | 0.665 | 0.633 |
| 360 | 0.590 | 0.259 |

As depicted in Table 2, the pyrazolopyrimidinone compound of formula 1 showed larger affinities for the urogenital organs than the sildenafil. Moreover, the sildenafil concentrations in the organs reached the peak were rapidly decreased as time went by, however, the pyrazolopyrimidinone compound of formula 1 concentrations in the organs were not decreased remarkably from the peak concentrations even though six hours passed. Particularly, it could be seen that the pyrazolopyrimidinone compound of formula 1 concentrations in the organs were kept two times than the sildenafil even though six hours passed.

Accordingly, the pyrazolopyrimidinone compound of formula 1 in accordance with the present invention can be used effectively and safely as an agent for preventing and treating the benign prostatic hyperplasia (BPH) and lower urinary tract symptoms (LUTS) associated with BPH or a relaxant for relaxing the urethral smooth muscle or the prostatic smooth muscle.

Example 4

Pharmacokinetic Experiment of Pyrazolopyrimidinone Compound in the Human Body

Among the volunteers of BPH patients aged 45 to 65 years, those who weighed above 45 kg and within a deviation of 15% in ideal body weights, voluntarily decided to participate in the experiment, consented by written, were reliable and would willingly aid the experiment and observe the restrictions were selected and randomly separated, to which 100, 50 and 10 mg of the pyrazolopyrimidinone compound of formula 1 and the sildenafil were administrated, respectively. The participants were all ten, five participants were administrated with the pyrazolopyrimidinone compound of formula 1 and the other five were administrated with the sildenafil.

The test was carried out in a double-blind manner and the participants were administrated with the test drugs with 240 ml of water at 8:00 to 9:00 am of the test day. After administration, all participants were fasted for four hours. After the fast, they were served a lunch of standard diet and provided a dinner of standard diet nine hours after the lunch. Blood collections were carried out before administrating the test drugs and 0.5, 1, 1.5, 2, 2.5, 3, 4, 5, 6, 8, 12 and 24 hours after the administration on the test day. From the bloods collected, blood plasmas were separated and analyzed using high performance liquid chromatography (HPLC). 100 ml of 0.1 M sodium carbonate and 1.0 ml of ethylether were added to each 0.5 ml of blood plasma and mixed well for one minute. Then, the resultant solutions were centrifuged at 12,000 ppm for three minutes. Subsequently, the supernatants were collected, from which organic solvents were volatilized using a Speed-Vac, to which 100 ml of mobile phases were added, stirred and injected into the high performance liquid chromatography (HPLC). The results were shown in Table 3 below.

TABLE 3

|  | Compound of formula 1 (100 mg) | Sildenafil (50 mg) |
| --- | --- | --- |
| Half-life (time) | 12.1 ± 3.2[a] | 4.1 ± 1.1 |

[a]Average ± Standard deviation

As shown in Table 3, the half-life of the compound of formula 1 was about 9 to 15 hours, which was longer three times than 3 to 5 hours of the sildenafil. Accordingly, it can be learned that since the compound of formula of the present invention has a half-life longer than the other PDE-5 inhibitors, the number of administration can be reduced, and thus increasing the administration compliance for the patients of the benign prostatic hyperplasia (BPH) and the lower urinary tract symptoms (LUTS) associated with BPH.

Hereinafter, various pharmaceutical preparations for the treatment drugs in accordance with the present invention will now be exemplified.

Preparation Example

Pharmaceutical Preparation for Oral Administration

1. Preparation of Powders

| Pyrazolopyrimidinone compound of formula 1 | 2 g |
| --- | --- |
| Lactose | 1 g |

The above ingredients were mixed with each other and packed in an airtight bag, thus preparing the powders.

2. Preparation of Tablets

| Pyrazolopyrimidinone compound of formula 1 | 100 mg |
| --- | --- |
| Corn starch | 100 mg |
| Lactose | 100 mg |
| Magnesium stearate | 2 mg |

The above ingredients were mixed with one another to prepare a tablet according to an ordinary method of preparing tablets 3. Preparation of Capsule

| Pyrazolopyrimidinone compound of formula 1 | 100 mg |
| --- | --- |
| Corn starch | 100 mg |
| Lactose | 100 mg |
| Magnesium stearate | 2 mg |

The above ingredients were mixed with one another to prepare a capsule in a gelatin capsule according to an ordinary method of preparing capsules.

Although the present invention has been described with reference to certain exemplary embodiments thereof, it will be understood by those skilled in the art that a variety of modifications may be made therein without departing from the spirit or scope of the present invention defined by the appended claims and their equivalents.

INDUSTRIAL APPLICABILITY

The agent for preventing and treating the benign prostatic hyperplasia (BPH) and the lower urinary tract symptoms (LUTS) associated with BPH and the relaxant for relaxing the urethral smooth muscle or the prostatic smooth muscle, both comprising the pyrazolopyrimidinone compound as an effective ingredient, cause fewer side effects, improve patient compliance and reduce the frequency of administration since its half-life is longer, compared with the other PDE-5 inhibitors having the same mechanism, thus being applicable industrially.

What is claimed is:

1. A method for treating benign prostatic hyperplasia (BPH) or a BPH associated symptom comprising administering an effective amount of a compound of Formula 1

[Formula 1]

to a subject in need thereof.

2. The method of claim 1, wherein the BPH associated symptom is lower urinary tract symptom (LUTS).

3. The method of claim 1, wherein the compound of Formula 1 relaxes prostatic smooth muscle or urethral smooth muscle.

4. The method of claim 1, wherein the compound of Formula 1 lowers intraurethral pressure (IUP).

5. The method of claim 1, wherein the compound of Formula 1 inhibits an activity of PDE-5.

6. The method of claim 1, wherein the compound of Formula 1 does not inhibit the activity of PDE-11 but inhibits an activity of PDE-5.

7. The method of claim 1, wherein the compound of Formula 1 does not cause testicle toxicity or myalgia, since it does not have an inhibitory action for the activity of PDE-11.

8. The method of claim 1, wherein the compound of Formula 1 is effective for 12 to 24 hours with a low frequency of administration.

9. The method of claim 1, wherein a maximum blood concentration of the compound of Formula 1 is reached within 50 to 70 minutes.

10. The method of claim 1, wherein a half-life of the compound of Formula 1 is 9 to 15 hours.

* * * * *